United States Patent [19]

Morita et al.

[11] Patent Number: 5,684,186
[45] Date of Patent: Nov. 4, 1997

[54] PROCESS FOR PRODUCTION OF PHENYLLACTIC ACID DERIVATIVE

[75] Inventors: Hikari Morita; Hiroyuki Mori, both of Kanagawa, Japan

[73] Assignee: Nitto Chemical Industry Co., Ltd., Tokyo, Japan

[21] Appl. No.: 511,152

[22] Filed: Aug. 4, 1995

[30] Foreign Application Priority Data

Aug. 9, 1994 [JP] Japan ................................ 6-206102

[51] Int. Cl.$^6$ ........................................... C07C 65/10
[52] U.S. Cl. ................................. 562/470; 560/60
[58] Field of Search .................... 562/470; 560/60

[56] References Cited

FOREIGN PATENT DOCUMENTS

A20295890  12/1988  European Pat. Off. .

971429  1/1951  France .

OTHER PUBLICATIONS

Synthesis, 793 (1992).
Z. fur. Physior. Chemie, vol. 65, 398 (1910).

Primary Examiner—Paul J. Killos
Attorney, Agent, or Firm—Sughrue, Mion, Zinn, Macpeak & Seas, PLLC

[57] ABSTRACT

A process for producing a phenyllactic acid derivative comprises hydrogenating a phenylpyruvic acid derivative in the presence of a catalyst containing at least one element selected from the Group VIII elements of the periodic table. The process provides a phenyllactic acid derivative useful as an intermediate in the production of pharmaceuticals and agricultural chemicals. The process uses as a starting material a phenylpyruvic acid derivative which is easily synthesized. The process is simpler in operation and provides a higher yield than conventional processes.

4 Claims, No Drawings

PROCESS FOR PRODUCTION OF PHENYLLACTIC ACID DERIVATIVE

FIELD OF THE INVENTION

The present invention relates to a process for producing a phenyllactic acid derivative represented by formula (1):

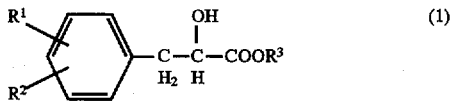

wherein $R^1$ and $R^2$, which may be the same or different, each represents a hydrogen atom, a hydroxyl group, a straight-chain or branched alkyl group having 1 to 4 carbon atoms or a straight-chain or branched alkoxy group having 1 to 4 carbon atoms, or $R^1$ and $R^2$ are linked to form a methylenedioxy group; and $R^3$ represents a hydrogen atom or a straight-chain or branched alkyl group having 1 to 3 carbon atoms, which is useful as an intermediate in the production of pharmaceuticals and agricultural chemicals.

BACKGROUND OF THE INVENTION

Well-known processes for producing phenyllactic acid derivatives include a process of reacting an α-amino acid with nitrous acid, a process comprising conversion of an aldehyde to a cyanohydrin followed by hydrolysis of the nitrile moiety, a process comprising halogenation of the α-position of a carboxylic acid followed by hydrolysis, a process comprising reduction of phenylpyruvic acid, and a process comprising reacting a Grignard reagent prepared from a halogenated benzene derivative and magnesium with glycidic acid or an ester thereof.

For example, known processes for producing 3-(4-hydroxyphenyl)lactic acid include (1) a process comprising reacting L-tyrosine and nitrous acid (Z. fur. Physior. Chemie, Vol. 65, 398 (1910)) and (2) a process comprising reducing 3-(4-hydroxyphenyl)pyruvic acid with Zn-Hg (Synthesis, 793 (1992)).

Process (1) is inferior in yield, achieving only 10% yield or even less, and is accompanied by production of a large amount of a by-product, which requires complicated operations for isolation and purification of the product. Process (2) imposes great restrictions on the manner of operation and disposal of the waste because of the use of poisonous Hg and is therefore unsuitable for industrial production.

The above-described general process comprising conversion of an aldehyde to a cyanohydrin followed by hydrolysis is applicable, though unreported in the literature, to production of 3-(4-hydroxyphenyl)lactic acid. However, since the starting material, i.e., 4-hydroxyphenylacetaldehyde, is not easily available, it must be synthesized separately through a complicated process, which increases the number of steps involved.

The process comprising halogenation of the α-position of a carboxylic acid followed by hydrolysis is disadvantageous in that the starting 3-(4-hydroxyphenyl)propionic acid is not easily available and that a highly corrosive phosphorous halide must be used, which imposes a great restriction on the material of the apparatus.

The process of reacting a Grignard reagent with glycidic acid or an ester thereof is disadvantageous in that the starting glycidic acid or ester thereof is not easily available and must be synthesized separately. Besides, it is difficult to isolate and purify glycidic acid due to its low stability. The other starting material, that is, the Grignard reagent, must be used in an amount 3 to 4 times the amount of the glycidic acid. This is economically disadvantageous.

SUMMARY OF THE INVENTION

The present invention solves the above-mentioned problems associated with conventional techniques.

An object of the present invention is to provide a process for producing a phenyllactic acid derivative in high yield by catalytic hydrogenation with a phenylpyruvic acid derivative that can easily be prepared as a starting material.

In order to accomplish the above object, the present inventors have conducted extensive investigations and, as a result, have found that a phenyllactic acid derivative can be produced in high yield by catalytic hydrogenation of a phenylpyruvic acid derivative in the presence of a catalyst and thus reached the present invention.

The present invention relates to a process for producing a phenyllactic acid derivative represented by formula (1):

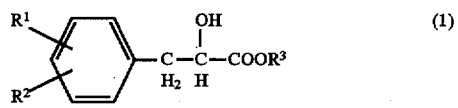

wherein $R^1$ and $R^2$, which may be the same or different, each represents a hydrogen atom, a hydroxyl group, a straight-chain or branched alkyl group having 1 to 4 carbon atoms or a straight-chain or branched alkoxy group having 1 to 4 carbon atoms, or $R^1$ and $R^2$ are linked to form a methylenedioxy group; and $R^3$ represents a hydrogen atom or a straight-chain or branched alkyl group having 1 to 3 carbon atoms, which comprises hydrogenating a phenylpyruvic acid derivative represented by formula (2):

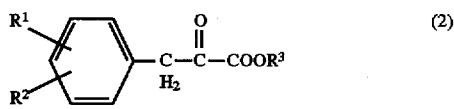

wherein $R^1$ and $R^2$, which may be the same or different, each represents a hydrogen atom, a hydroxyl group, a straight-chain or branched alkyl group having 1 to 4 carbon atoms or a straight-chain or branched alkoxy group having 1 to 4 carbon atoms, or $R^1$ and $R^2$ are linked to form a methylenedioxy group; and $R^3$ represents a hydrogen atom or a straight-chain or branched alkyl group having 1 to 3 carbon atoms, in the presence of a catalyst.

DETAILED DESCRIPTION OF THE INVENTION

The present invention is explained in detail below.

The phenylpyruvic acid derivative which can be used as a starting material in the process of the present invention is represented by formula (2):

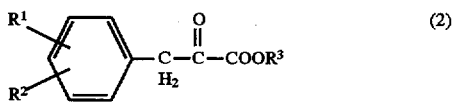

wherein $R^1$ and $R^2$, which may be the same or different, each represents a hydrogen atom, a hydroxyl group, a straight-chain or branched alkyl group having 1 to 4 carbon atoms or a straight-chain or branched alkoxy group having 1 to 4 carbon atoms, or $R^1$ and $R^2$ are linked to form a methylenedioxy group; and $R^3$ represents a hydrogen atom or a straight-chain or branched alkyl group having 1 to 3 carbon atoms.

Specific examples of the phenylpyruvic acid derivative represented by formula (2) are 3-phenylpyruvic acid, isopropyl 3-phenylpyruvate, 3-(4-hydroxyphenyl)pyruvic acid, methyl 3-(4-hydroxyphenyl)pyruvate, ethyl 3-(4-hydroxyphenyl)pyruvate, isopropyl 3-(4-hydroxyphenyl) pyruvate, 3-(4-methoxyphenyl)pyruvic acid, 3-(4-ethoxyphenyl)pyruvic acid, methyl 3-(4-methoxyphenyl) pyruvate, 3-(4-methylphenyl)pyruvic acid, methyl 3-(4-methylphenyl)pyruvate, 3-(4-t-butylphenyl)pyruvic acid, 3-(3,4-methylenedioxyphenyl)pyruvic acid, methyl 3-(3,4-methylenedioxyphenyl)pyruvate, 3-(3-hydroxyphenyl) pyruvic acid, ethyl 3-(3-hydroxyphenyl)pyruvate, 3-(3-methoxyphenyl)pyruvic acid, isopropyl 3-(3-methoxyphenyl)pyruvate, 3-(3-methylphenyl)pyruvic acid, methyl 3-(3-methylphenyl)pyruvate, 3-(2-hydroxyphenyl) pyruvic acid, ethyl 3-(2-hydroxyphenyl)pyruvate, 3-(2-methoxyphenyl)pyruvic acid, isopropyl 3-(2-methoxyphenyl)pyruvate, 3-(2-methylphenyl)pyruvic acid, methyl 3-(2-methylphenyl)pyruvate, 3-(3,4-dihydroxyphenyl)pyruvic acid, methyl 3-(3,4-dihydroxyphenyl)pyruvate, 3-(3,4-dimethoxyphenyl) pyruvic acid, ethyl 3-(3,4-dimethoxyphenyl)pyruvate, 3-(3-hydroxy-4-methoxyphenyl)pyruvic acid, ethyl 3-(3-hydroxy-4-methoxyphenyl)pyruvate, 3-(4-hydroxy-3-methylphenyl)pyruvic acid, and methyl 3-(4-hydroxy-3-methylphenyl)pyruvate.

The phenylpyruvic acid derivative to be used as a starting material can easily be obtained by hydrolyzing a benzylideneoxazolinone derivative, produced from a benzaldehyde derivative and N-acetylglycine, with an acid (Henry N. C. Wong, *Synthesis*, 793 (1992)).

The catalyst which can be used in the present invention contains at least one element selected from the Group VIII elements of the periodic table, preferably at least one element selected from cobalt, nickel, rhodium, palladium, and platinum. The element selected can be used as a catalyst either as a metal or in the form of a compound, such as a salt (e.g., nitrate, sulfate or chloride), an oxide or a hydroxide. The element may also be used as supported on a carrier. Suitable carriers include activated carbon, silica gel, and alumina. A suitable amount of the element to be supported on a carrier is 5 to 70% by weight. Examples of suitable catalysts include palladium-carbon (palladium on charcoal), platinum oxide, Raney nickel, rhodium, palladium, platinum, platinum-carbon (platinum on charcoal), rhodium-platinum oxide, and cobalt-silica gel.

The catalyst is used in an amount usually of from 1/5 to 1/1000, preferably of from 1/10 to 1/100, of the weight of the starting phenylpyruvic acid derivative.

Any solvent can be used in the reaction, provided that the starting phenylpyruvic acid derivative is soluble therein. Examples of suitable solvents include aliphatic alcohols, such as methanol, ethanol, isopropyl alcohol, and ethylene glycol; aliphatic ethers, such as dimethoxyethane, dioxane, and tetrahydrofuran; aliphatic esters, such as methyl acetate, ethyl acetate, and ethyl propionate; and aromatic hydrocarbons, such as toluene and xylene. Aliphatic alcohols are particularly preferred for reduction of the reaction time.

While the process of the present invention usually requires no heating, the reaction may be conducted under heating. The reaction is carried out at a temperature ranging from 0° to 100° C. and a hydrogen pressure ranging from 1 to 100 kg/cm², preferably 1 to 30 kg/cm². The reaction time is usually within 12 hours, e.g., from 0.5 to 8 hours, while varying according to the reaction conditions, such as catalyst amount, reaction temperature, hydrogen pressure, and the like.

The present invention will now be illustrated in greater detail by way of a Reference Example and Examples, but should not be construed as being limited thereto.

Synthesis of the starting phenylpyruvic acid derivative is illustrated in the Reference Example.

REFERENCE EXAMPLE

Synthesis of 3-(4-Hydroxyphenyl)pyruvic Acid 3-(4-Hydroxyphenyl)pyruvic acid was synthesized through the following three steps (a), (b), and (c).

(a) 12.2 g of 4-hydroxybenzaldehyde, 13.9 g of N-acetylglycine, 15.6 g of sodium acetate, and 51.0 g of acetic anhydride were mixed, and the mixture was stirred at 120° C. for 5 hours. After the reaction, the reaction mixture was cooled to room temperature, and 50 ml of ice-water was added thereto, followed by stirring for 1 hour. The precipitated crystals were collected by filtration and washed with 100 ml of water. The resulting crystals were vacuum dried to give 22.0 g of 4-(4-acetoxybenzylidene)-2-methyloxazol-5(4H)-one as yellow crystals.

(b) 20 g of 4-(4-acetoxybenzylidene)-2-methyloxazol-5(4H)-one were suspended in 800 ml of 0.2N hydrochloric acid, and the suspension was stirred at 100° C. for 0.5 hours. After the reaction, the reaction mixture was cooled to room temperature. The precipitated crystals were collected by filtration to give 16.1 g of 2-acetylamino-3-(4-hydroxyphenyl)cinnamic acid as pale yellow crystals.

(c) 11.1 g of 2-acetylamino-3-(4-hydroxyphenyl) cinnamic acid were suspended in 300 ml of 3N hydrochloric acid, and the suspension was stirred at 80° C. for 6 hours. After the reaction, the reaction mixture was cooled to room temperature. The precipitated crystals were collected by filtration. The filtrate was concentrated to about 1/3 by volume, and the precipitated crystals were collected by filtration. All the crystals were combined, washed with 50 ml of water, and dried in vacuo to obtain 7.1 g of 3-(4-hydroxyphenyl)pyruvic acid as colorless crystals.

EXAMPLE 1

10 g of 3-(4-hydroxyphenyl)pyruvic acid and 50 ml of methanol were charged to a pressure reactor to form a solution, and 0.5 g of 5% palladium on charcoal was added thereto. The atmosphere was displaced with hydrogen, and the mixture was stirred at 25° C. under a hydrogen pressure of 5 kg/cm² for 2 hours. After completion of the reaction, the reaction mixture was filtered to remove the catalyst, and the filtrate was concentrated under reduced pressure to give 10.1 g of 3-(4-hydroxyphenyl)lactic acid as colorless crystals.

EXAMPLE 2

10 g of 3-(4-hydroxyphenyl)pyruvic acid were dissolved in 50 ml of isopropyl alcohol, and 0.3 g of 10% palladium on charcoal was added thereto. The mixture was stirred at 25° C. under atmospheric pressure for 6 hours in a hydrogen stream. After completion of the reaction, the catalyst was removed by filtration, and the filtrate was concentrated under reduced pressure to give 9.8 g of 3-(4-hydroxyphenyl) lactic acid as colorless crystals.

EXAMPLE 3

10 g of 3-(4-hydroxyphenyl)pyruvic acid were dissolved in 50 ml of methanol, and 0.05 g of platinum oxide was added thereto. The mixture was stirred at 25° C. under atmospheric pressure for 6 hours in a hydrogen stream. After completion of the reaction, the catalyst was removed by filtration, and the filtrate was concentrated under reduced pressure to give 10.1 g of 3-(4-hydroxyphenyl)lactic acid as colorless crystals.

EXAMPLE 4

10 g of 3-(4-hydroxyphenyl)pyruvic acid and 50 ml of ethanol were charged to a pressure reactor to form a solution, and 1.0 g of Raney nickel was added thereto. The atmosphere was displaced with hydrogen, and the mixture was stirred at 70° C. under a hydrogen pressure of 30 kg/cm² for 0.5 hour. After completion of the reaction, the reaction mixture was filtered to remove the catalyst, and the filtrate was concentrated under reduced pressure to give 8.7 g of 3-(4-hydroxyphenyl)lactic acid as colorless crystals.

EXAMPLE 5

10 g of 3-(4-hydroxyphenyl)pyruvic acid and 50 ml of dioxane were charged to a pressure reactor to form a solution, and 0.5 g of 5% palladium on charcoal was added thereto. The atmosphere was displaced with hydrogen, and the mixture was stirred at 70° C. under a hydrogen pressure of 5 kg/cm² for 6 hours. After completion of the reaction, the reaction mixture was filtered to remove the catalyst, and the filtrate was concentrated under reduced pressure to give 10.0 g of 3-(4-hydroxyphenyl)lactic acid as colorless crystals.

EXAMPLES 6 to 15

The same procedure as in Example 1 was repeated, except for replacing 3-(4-hydroxyphenyl)pyruvic acid with each of the phenylpyruvic acid derivatives shown below, to obtain a corresponding phenyllactic acid derivative in the yield shown in Table 1.

TABLE 1

| Example No. | Phenylpyruvic Acid Derivative | Reaction Time (hr) | Yield (%) |
|---|---|---|---|
| 6 | 3-(4-methoxyphenyl)pyruvic acid | 2 | 98 |
| 7 | 3-(4-ethoxyphenyl)pyruvic acid | 2 | 97 |
| 8 | 3-(3-hydroxyphenyl)pyruvic acid | 3 | 95 |
| 9 | 3-(3,4-methylenedioxyphenyl)pyruvic acid | 2 | 93 |
| 10 | 3-(3,4-dihydroxyphenyl)pyruvic acid | 4 | 92 |
| 11 | 3-(2-hydroxyphenyl)pyruvic acid | 2 | 95 |
| 12 | 3-phenylpyruvic acid | 2 | 96 |
| 13 | 3-(4-methylphenyl)pyruvic acid | 2 | 97 |
| 14 | 3-(4-t-butylphenyl)pyruvic acid | 2 | 90 |
| 15 | 3-(3-hydroxy-4-methoxyphenyl)pyruvic acid | 3 | 93 |

EXAMPLE 16

10 g of ethyl 3-(4-hydroxyphenyl)pyruvate and 30 ml of toluene were charged to a pressure reactor to form a solution, and 0.25 g of 5% palladium on charcoal was added thereto. The atmosphere was displaced with hydrogen, and the mixture was stirred at 50° C. under a hydrogen pressure of 5 kg/cm² for 1 hour. After completion of the reaction, the reaction mixture was filtered to remove the catalyst, and the filtrate was concentrated under reduced pressure to give 9.9 g of ethyl 3-(4-hydroxyphenyl)lactate as a colorless oily substance.

EXAMPLES 17 to 20

The same procedure as in Example 16 was repeated, except for replacing ethyl 3-(4-hydroxyphenyl)pyruvate with each of the phenylpyruvic acid derivatives shown below, to obtain a corresponding phenyllactic acid derivative in the yield shown in Table 2.

TABLE 2

| Example No. | Phenylpyruvic Acid Derivative | Reaction Time (hr) | Yield (%) |
|---|---|---|---|
| 17 | methyl 3-(4-methoxyphenyl)pyruvate | 2 | 98 |
| 18 | isopropyl 3-phenylpyruvate | 1 | 95 |
| 19 | methyl 3-(3,4-methylenedioxyphenyl)pyruvate | 2 | 93 |
| 20 | ethyl 3-(3-hydroxyphenyl)pyruvate | 1 | 94 |

According to the process of the present invention, a phenylpyruvic acid derivative which can be obtained by an easy synthesis route can be converted to a phenyllactic acid derivative in high yield by hydrogenation in the presence of a catalyst. Requiring neither high pressure nor high temperature, the process of the present invention requires no special operation or equipment and is therefore suitable for large-scale production.

While the invention has been described in detail and with reference to specific embodiments thereof, it will be apparent to one skilled in the art that various changes and modifications can be made therein without departing from the spirits and scope thereof.

What is claimed is:

1. A process for producing a phenyllactic acid derivative represented by formula (1):

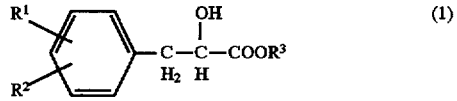

wherein R¹ and R², which may be the same or different, each represents a hydrogen atom, a hydroxyl group, a straight-chain or branched alkyl group having 1 to 4 carbon atoms or a straight-chain or branched alkoxy group having 1 to 4 carbon atoms, or R¹ and R² are linked to form a methylenedioxy group; and R³ represents a hydrogen atom or a straight-chain or branched alkyl group having 1 to 3 carbon atoms, which comprises hydrogenating a phenylpyruvic acid derivative represented by formula (2):

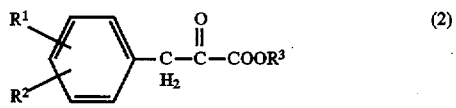

wherein R¹ and R², which may be the same or different, each represents a hydrogen atom, a hydroxyl group, a straight-chain or branched alkyl group having 1 to 4 carbon atoms or a straight-chain or branched alkoxy group having 1 to 4 carbon atoms, or R¹ and R² are linked to form a methylenedioxy group; and R³ represents a hydrogen atom or a straight-chain or branched alkyl group having 1 to 3 carbon atoms, in the presence of a catalyst comprising at least one element selected from the group consisting of palladium, platinum, rhodium and cobalt.

2. The process of claim 1, wherein the catalyst is palladium-carbon, platinum oxide, rhodium, palladium, platinum, platinum-carbon, rhodium-platinum oxide or cobalt-silica gel.

3. The process of claim 1, wherein the catalyst is palladium-carbon.

4. The process of claim 1, wherein the catalyst is platinum oxide.

* * * * *